US00PP09108P

United States Patent [19]

VandenBerg

[11] Patent Number: Plant 9,108

[45] Date of Patent: Apr. 18, 1995

[54] CHRYSANTHEMUM PLANT NAMED FARGO

[75] Inventor: Cornelis P. VandenBerg, Salinas, Calif.

[73] Assignee: Yoder Brothers, Inc., Barberton, Ohio

[21] Appl. No.: 277,285

[22] Filed: Jul. 21, 1994

[51] Int. Cl.[6] ..... A01H 5/00

[52] U.S. Cl. ..... Plt./82.2

[58] Field of Search ..... Plt. 82.2, 74.1

*Primary Examiner*—Howard J. Locker

*Attorney, Agent, or Firm*—Foley & Lardner

[57] ABSTRACT

A Chrysanthemum plant named Fargo particularly characterized by its flat capitulum form; daisy capitulum type; yellow ray floret color with a strong bronze overcast on the underside of the ray florets; diameter across face of capitulum of 32 to 38 mm when fully opened, when grown as a single stem spray cut mum; flowering response under normal temperatures of 50 to 53 days after start of short days; plant height of 74 to 79 cm with 18 long days prior to start of short days; peduncle length of the first lateral at flowering after removing the apical bud and without growth regulator applications of 5 to 8 cm, and peduncle length of the fourth lateral at flowering of 8 to 10 cm; and terminal spray formation, with lower laterals being compound.

3 Drawing Sheets

The present invention comprises a new and distinct cultivar of Chrysanthemum, botanically known as *Dendranthema grandiflora,* and referred to by the cultivar name Fargo.

Fargo, identified as 3075 (90-547004), was originated from a cross made by Cornelis P. VanderBerg in a controlled breeding program in Salinas, Calif., in 1989.

The female parent of Fargo was an unpatented commercial cultivar identified as Aria, and described as a flat daisy spray cut mum with a yellow ray floret color; a diameter of capitulum of 32 to 38 mm; a flowering response in Salinas, Calif. of 53 to 57 days; a plant height of 84 to 92 cm when grown with 11 to 14 long days prior to start of short days in Salinas, Calif.; a peduncle length of the first lateral of 10 to 13 cm and of the fourth lateral of 13 to 18 cm; and a terminal spray formation, with lower laterals being compound.

The male parent of Fargo was an unnamed seedling, identified as 2064 (87-461001), and described as a flat daisy spray cut mum with a light pink ray floret color; a diameter of capitulum of 41 to 48 mm; flowering response to short days of 51 to 57 days in Salinas, Calif.; a plant height of 97 to 107 cm with 7 to 14 long days prior to start of short days; a peduncle length of the first lateral of 10 cm and of the fourth lateral of 15 cm; and a terminal spray formation with lower laterals being compound. The male parent was discarded from all programs on Nov. 9, 1990.

Fargo was discovered and selected as one flowering plant within the progeny of the stated cross by Cornelis P. VandenBerg in Oct. 1990, in a controlled environment in Salinas, Calif.

The first act of asexual reproduction of Fargo was accomplished when vegetative cuttings were taken from the initial selection in Dec. 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Fargo are firmly fixed and are retained through successive generations of asexual reproduction.

Fargo has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., under greenhouse conditions which approximate those generally used in commercial greenhouse practice.

The following traits have been repeatedly observed and are determined to be basic characteristics of Fargo, which, in combination, distinguish the Chrysanthemum as a new and distinct cultivar:

1. Flat capitulum form.
2. Daisy capitulum type.
3. Yellow ray floret color with a strong bronze overcast on the underside of the ray florets.
4. Diameter across face of capitulum of 32 to 38 mm when fully opened, when grown as a single stem spray cut mum.
5. Flowering response under normal temperatures if 50 to 53 days after start of short days.
6. Plant height is 74 to 79 cm with 18 long days prior to start of short days.
7. Peduncle length of the first lateral at flowering after removing the apical bud and without growth regulator applications is 5 to 8 cm. Peduncle length of the fourth lateral at flowering 8 to 10 cm.
8. Terminal spray formation, with lower laterals being compound.

The accompanying photographic drawings show typical inflorescence and leaf characteristics of Fargo, with the colors being as nearly true as possible with illustrations of this type.

Sheet 1 is a color photograph of Fargo grown as a single stem spray cut mum.

Sheet 2 is a black and white photograph of three views of the inflorescence of Fargo.

Sheet 3 is a black and white photograph showing the upper and under sides of the leaves of Fargo at three stages of development (mature, intermediate and immature).

In sheets 2 and 3 a measuring tape in centimeters has been added.

Of the commercial cultivars known to the inventor, the most similar in comparison to Fargo is the parent cultivar Aria. Reference is made to attached Chart A, which compares certain characteristics of Fargo to the same characteristics of Aria.

Similar traits are capitulum form and type, diameter of capitulum and spray formation. The underside of the ray florets of Fargo show a strong bronze overcast, while the ray florets of Aria are clear yellow. Fargo also has a faster flowering response to short days, a shorter plant height and shorter peduncles when compared with Aria.

In the following description color references are made to The Royal Horticultural Society Color Chart. The color values were determined on plant material grown as a single stem spray cut mum in Salinas, Calif. on Dec. 16, 1993.

Classification:

*Botanical.*—*Dendranthema grandiflora* cv Fargo.

*Commercial.*—Daisy spray cut mum.

INFLORESCENCE

A. Capitulum:

*Form.*—Flat.

*Type.*—Daisy.

*Diameter across face.*—32 to 38 mm when fully opened.

B. Corolla of ray florets:

*Color (general tonality from a distance of three meters).*—Yellow with bronze underside.

*Color (upper surface).*—7A.

*Color (under surface).*—7A, with strong bronze overcast.

*Shape.*—Straight, flat, slightly pointed

C. Corolla of disc florets:

*Color (mature).*—14A.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—74 to 79 cm when grown in Salinas with 18 long days prior to start of short days.

B. Foliage:

*Color (upper surface).*—147A.

*Color (under surface).*—147B.

*Shape.*—See photograph.

CHART A

COMPARISON OF FARGO AND ARIA

| CHARACTERISTIC | FARGO | ARIA |
|---|---|---|
| Ray floret color | Yellow with bronze underside | Yellow |
| Capitulum form and type | Flat daisy | Flat daisy |
| Diameter across face of capitulum | 32 to 38 mm | 32 to 38 mm |
| Flowering response | 50 to 53 days | 53 to 57 days |
| Plant height | | |
| with 18 long days | 74 to 79 cm | |
| with 11 to 14 long days | | 84 to 92 cm |
| Peduncle length | | |
| First lateral | 5 to 8 cm | 10 to 13 cm |
| Fourth lateral | 8 to 10 cm | 13 to 18 cm |
| Spray information | Terminal with lower laterals compound | Terminal with lower laterals compound |

COMPARISON MADE OF PLANTS GROWN AS SINGLE STEM SPRAY CUT MUMS IN SALINAS, CALIFORNIA

I claim:

1. A new and distinct Chrysanthemum plant named Fargo, as described and illustrated.

* * * * *

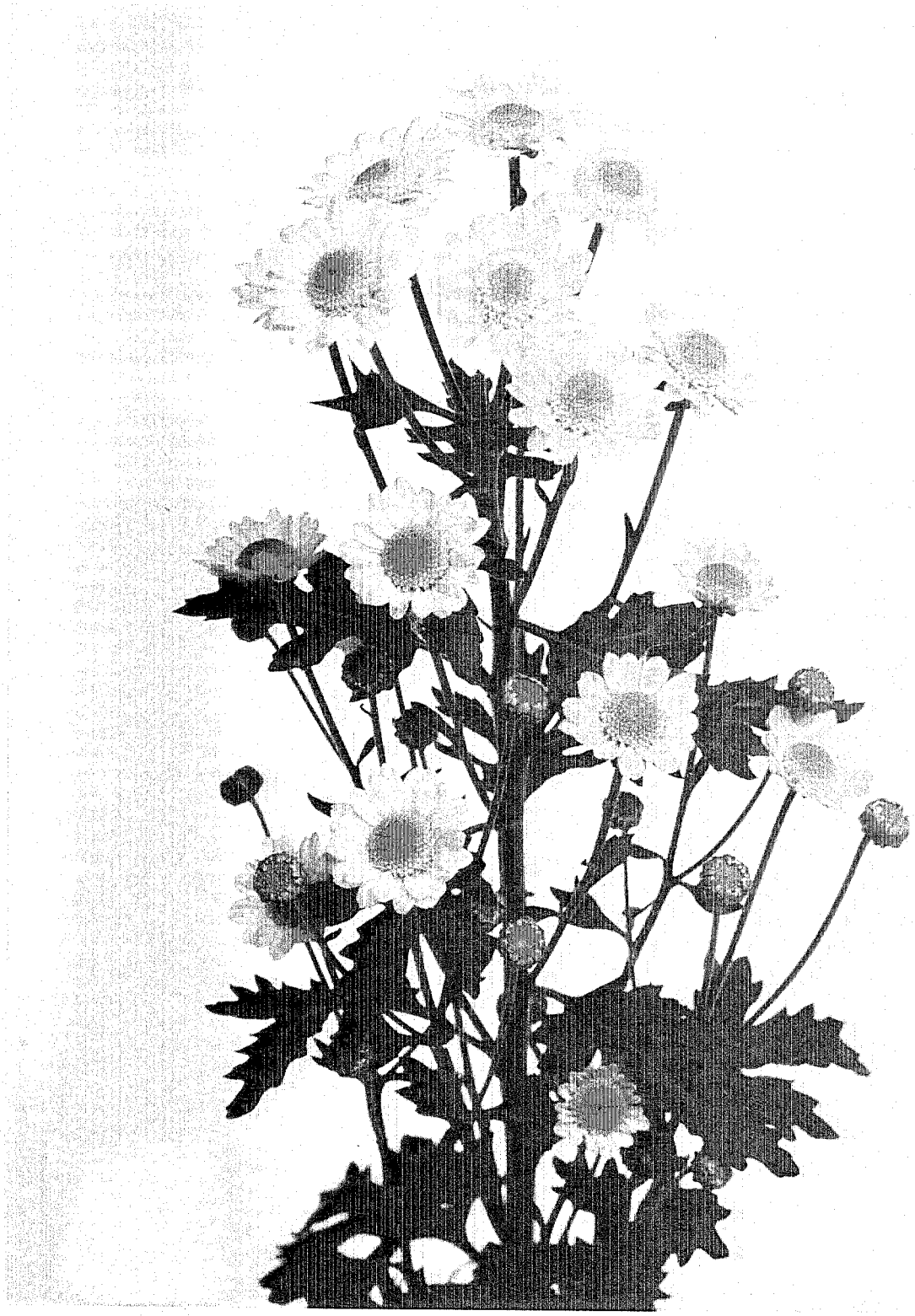

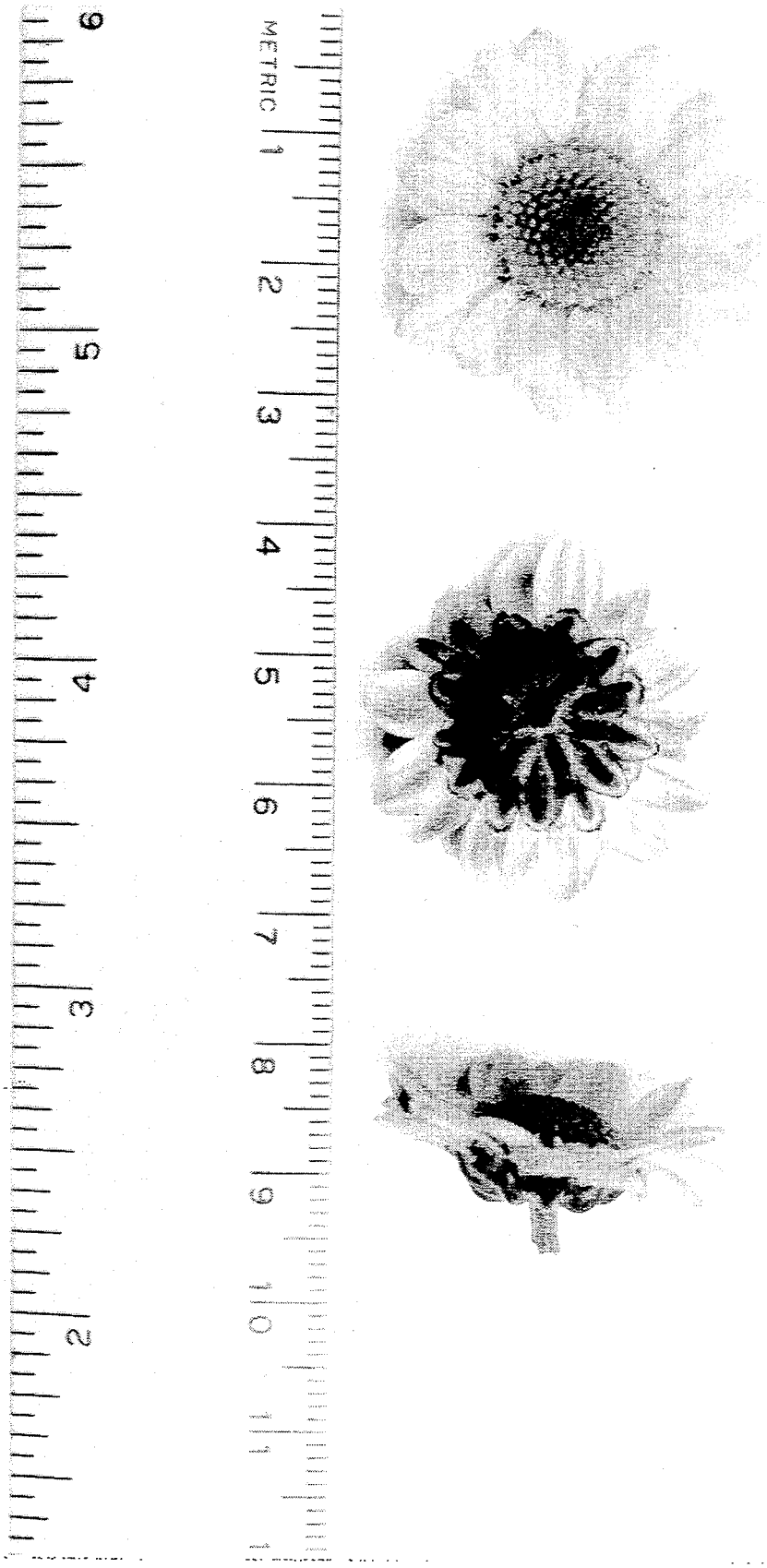
METRIC

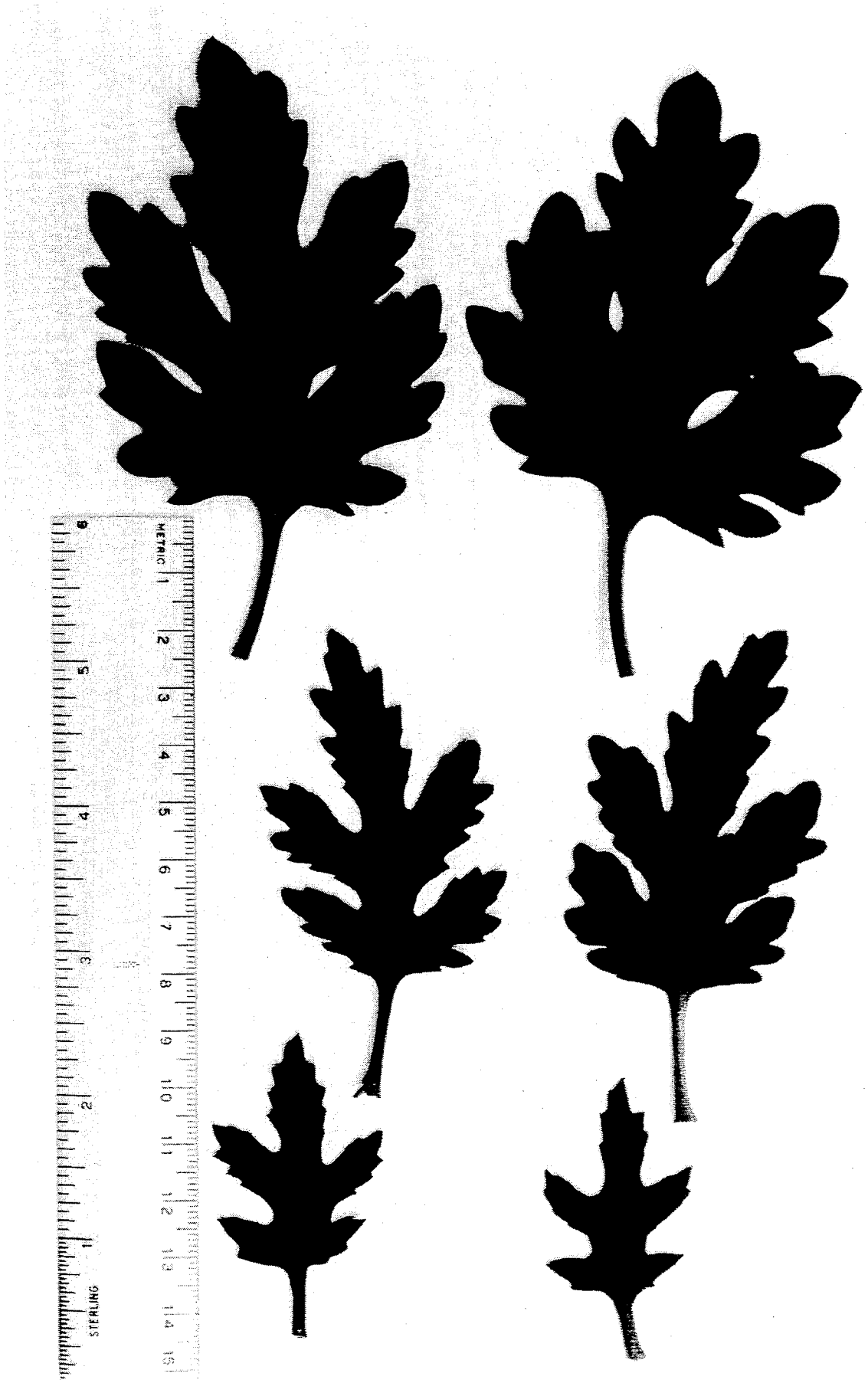
STERLING
METRIC